(12) United States Patent
Griesbach et al.

(10) Patent No.: US 8,323,981 B2
(45) Date of Patent: Dec. 4, 2012

(54) INDUCTION FURNACE OPERATING IN A RANGE FROM 2-9 MHZ FOR PROVIDING ANALYTICAL SAMPLES AND METHOD OF SAME

(75) Inventors: Jason Griesbach, Richfield, WI (US); Ted Casper, West Bend, WI (US)

(73) Assignee: Leco Corporation, St. Joseph, MI (US)

( * ) Notice: Subject to any disclaimer, the term of this patent is extended or adjusted under 35 U.S.C. 154(b) by 133 days.

(21) Appl. No.: 12/894,480

(22) Filed: Sep. 30, 2010

(65) Prior Publication Data
US 2012/0083042 A1  Apr. 5, 2012

(51) Int. Cl.
*G01N 25/22* (2006.01)

(52) U.S. Cl. ........ 436/159; 436/155; 373/138; 373/156; 373/163; 373/139

(58) Field of Classification Search .................... 422/78; 436/159, 155; 373/138, 156, 163, 139
See application file for complete search history.

(56) References Cited

U.S. PATENT DOCUMENTS

| | | | | | |
|---|---|---|---|---|---|
| 2,809,100 | A | * | 10/1957 | Krasl | 422/80 |
| 3,392,970 | A | * | 7/1968 | Falk | 432/262 |
| 3,878,073 | A | * | 4/1975 | Boorstein et al. | 205/705 |
| 3,985,505 | A | * | 10/1976 | Bredeweg | 436/160 |
| 4,392,230 | A | * | 7/1983 | Keller et al. | 117/39 |

* cited by examiner

*Primary Examiner* — Krishnan S Menon
*Assistant Examiner* — Dwan A Gerido
(74) *Attorney, Agent, or Firm* — Price Heneveld LLP

(57) ABSTRACT

An analytical induction furnace and method for combusting conductive sample materials (500) utilizing a crucible for holding a sample within the induction furnace. Less than one gram of accelerator material is then inserted into the crucible with the sample and the induction furnace is activated for a predetermined time period (503) for thoroughly combusting the sample and accelerator. In some instances, no accelerator is required with the sample at frequencies of approximately 4.5 MHz. The invention provides for the induction furnace that is actuated in an RF frequency range between 2-9 MHz with little to no accelerator for thoroughly melting the sample for use in an analytical instrument.

15 Claims, 2 Drawing Sheets

INDUCTION FURNACE OPERATING IN A RANGE FROM 2-9 MHZ FOR PROVIDING ANALYTICAL SAMPLES AND METHOD OF SAME

FIELD OF THE INVENTION

The present invention generally relates to an induction furnace and more particularly to an induction furnace using a diminished amount of accelerator operating in a range from 2-9 MHz.

BACKGROUND OF THE INVENTION

An induction furnace is an electrical furnace in which the heat is applied by radio frequency (RF) induction to a conductive sample. FIG. 1 illustrates an induction furnace as used in the prior art. The sample 105 is placed in a non-conductive crucible 101, that is elevated on a pedestal 109 into a combustion tube 101 that has been purged with oxygen. Electrical alternating current energy is applied to the induction coil 107, which in turn induces high currents in the conductive sample. These high currents heat the sample to the point of melting, and some components of the metal may combust. The advantage of the induction furnace is that it is offers a clean, energy-efficient and well-controllable melting process compared to most other means of metal melting. In an analytical application, induction furnaces can be used to melt various types of metals including iron, steel, copper, aluminum, as well as precious metals. One major drawback to induction furnace usage is that the RF at which a sample is heated is not always optimal for a particular application.

In analytical applications, the historical operating frequency has typically remained in the range of about 13 MHz to 20 MHz, depending on the material being melted, and the output power capacity of the furnace. Prior art induction furnaces operate at a frequency that limits the types of samples that could be combusted. This was due to the "skin depth" of the sample which is a measure of the distance RF energy can penetrate beneath the surface of a conductor. For the same conductivity, higher frequency emission has a shallower skin depth that penetrates to a lesser depth into the sample, while lower frequencies can penetrate deeper into thicker samples.

FIG. 2 is a flow chart diagram illustrating the prior art process used in combusting materials using an induction furnace operating at 18 MHz. The process 200 of combusting metals in the induction furnace for analytical applications includes using a combustion accelerator that is inserted into the crucible with the metal sample. The accelerator plays an important role in proper combustion of the sample by an induction furnace. The purity and consistency of the accelerator is very important as it is typically low in both carbon and sulfur content. The role of the accelerator is to couple RF energy into the accelerator material, causing it to melt, which in turn couples thermal energy into the sample. If the sample reaches a critical temperature it will melt and evenly cover the bottom of the crucible, allowing for complete oxidation of any carbon or sulfur in the sample. Typically, one gram (1 g) of accelerator is used with each sample.

Initially in step 201, an accelerator is combusted (without a sample) and in step 202 the instrument determines the amount of analyte (such as carbon or sulfur) present in the accelerator. In step 203, the accelerator is then combined with the sample and is combusted in the induction furnace and analyzed in step 204. In step 205, a determination must be made if the sample was completely combusted. Preferably, the result should be a uniformly molten sample. In step 207, the amount of analyte in the accelerator can be mathematically subtracted from the results. In the event that the burn was not complete and/or uniform, a new sample must be combusted again which can be time consuming and expensive depending on the type of samples involved.

FIG. 3 is an illustration showing combusted samples using the processes described in FIG. 2. Samples 301, 303, 305 are of one type of material such as copper with each placed in its own crucible. The illustrations clearly show only partial burns of the material samples 301, 305 which are inconsistent between each of the samples. Similarly, samples 307, 309, 311 are another type of sample material such as nickel. These samples also show inconsistent and incomplete burns 311 between each of the samples that would require a new sample to be again combusted until an acceptable analysis is obtained.

FIG. 4 is a schematic illustrating an Colpitts induction oscillator circuit used in the induction furnace operating in a range between 13-20 MHz as shown in FIG. 1. In operation, electrical RF energy is coupled in through capacitor 401 to drive the circuit. The series combination of capacitors 403 and 407 form a resonant network with induction coil 405. The ratio of capacitors 403 and 407 set the amplitude of the feedback signal that is coupled through capacitor 409 to the drive circuit. In use, as the oscillator frequency drops, the inductive reactance of the coil 405 becomes substantially a low value that results in high currents which are on the order of 100 Amps. Consequently, the overall value of capacitance must increase as well as the physical size of the capacitors in order to handle these very high currents at low frequencies. Since capacitors 403 and 407 form a set ratio, capacitor 407 must be even larger in value and physical size.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
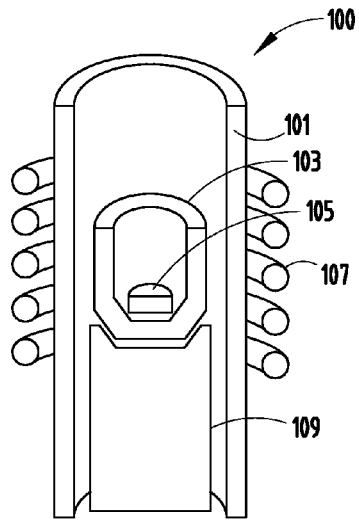
FIG. 1 is a prior art diagram illustrating a cut-away view of an induction furnace.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE PREFERRED EMBODIMENTS

Before describing in detail embodiments that are in accordance with the present invention, it should be observed that the embodiments reside primarily in combinations of method steps and apparatus components related to an induction furnace operating in a range from 2-9 MHz. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 2:
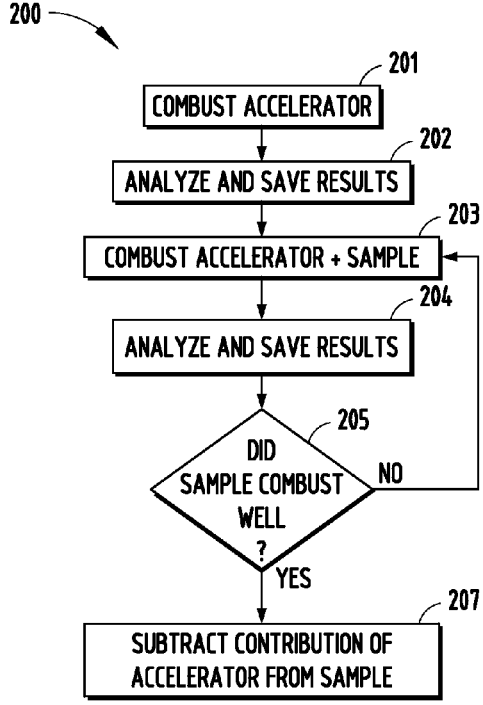
FIG. 2 is a flow chart diagram illustrating the process used in combusting materials using an induction furnace operating at 18 MHz.
Figure 5:
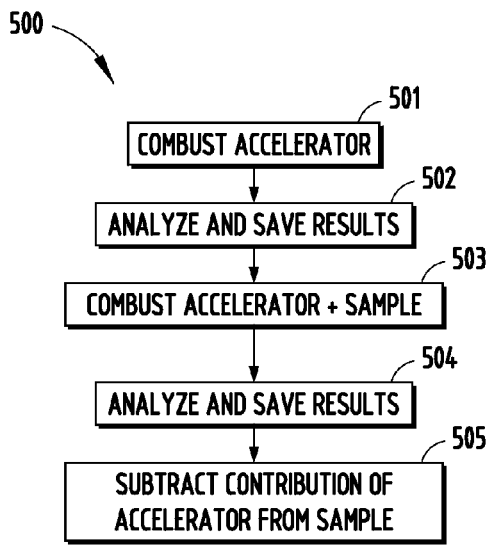
FIG. 5 is a flow chart illustrating the process used in combusting material using an induction furnace operating in a range between 2-9 MHz.

FIG. 5 is a flow chart illustrating the process used in combusting material using an induction furnace operating in a range between 2-9 MHz. The process 500 begins with a step 501 by placing a crucible containing accelerator in the RF induction furnace. As the accelerator is combusted without sample material, the analytical instrument records the amount of analyte released by the accelerator in step 502. The sample and accelerator are combined and combusted at a temperature such that the sample and accelerator are completely melted in step 503. The analytical instrument records the amount of analyte, such as carbon or sulfur, that is released by the combination of accelerator and sample in step 504. Thus in step 505, the contribution of the accelerator can be mathematically subtracted or removed from the level of analyte detected by the analytical instrument. The advantage of operating the induction furnace at this frequency is that the sample is completely melted with a more consistent combustion or burn. An additional advantage of this process is that the combustion is so efficient, particularly at 4.5 MHz, that the amount of accelerator required can be substantially diminished or eliminated completely when compared to the prior art process shown in FIG. 2. To enhance combustion, this process 500 can also include the step of combusting the sample in a substantially high oxygen environment.

Figure 3:
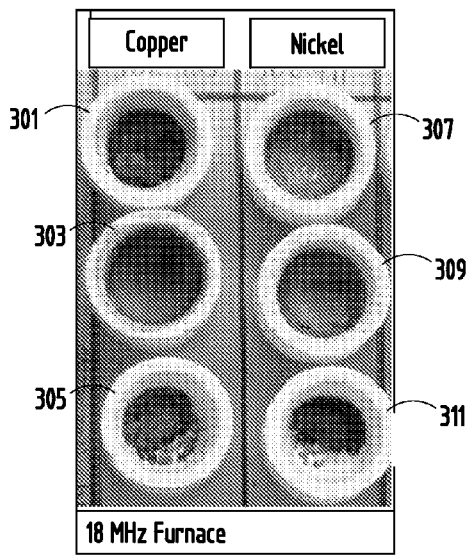
FIG. 3 is an illustration showing combusted samples using the processes described in FIG. 2.
Figure 4:
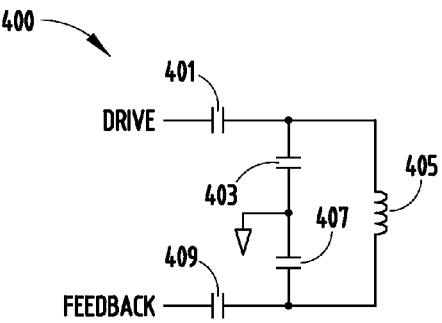
FIG. 4 is a schematic diagram illustrating an induction oscillator circuit as used in the prior art.
Figure 6:
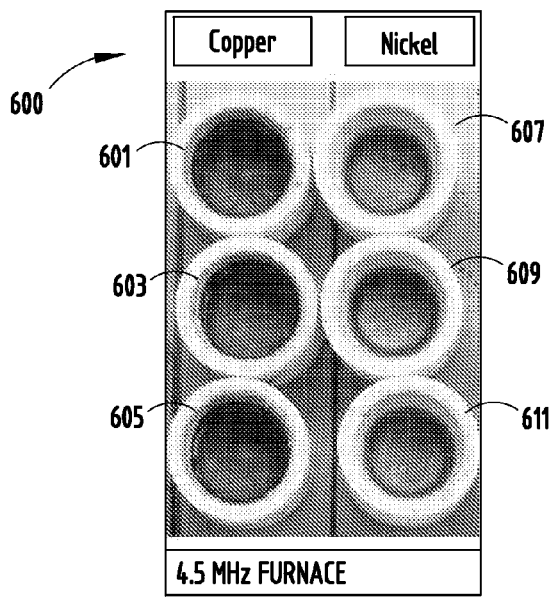
FIG. 6 is an illustration showing combusted samples using the process described in FIG. 5.

FIG. 6 is an illustration 600 showing combusted samples using the process described in FIG. 5. As compared to the samples shown in FIG. 3 that are combusted at 18 MHz, samples 601, 603, 605 are of one type of material such as copper with each placed in its own crucible. The illustrations clearly show a complete and thorough burn of the material between each of the samples. Similarly, samples 607, 609, 611 are a second type of material such as nickel. These samples also show a very consistent and complete combustion between each of the samples. Therefore, the process of providing an induction furnace operating in a range between 2-9 MHz is much more consistent and cost efficient since little or no samples need be re-combusted to complete the analysis.

Figure 7:
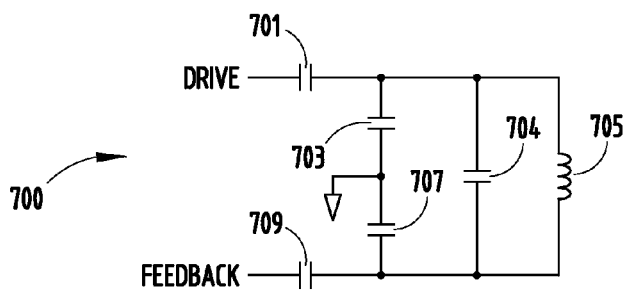
FIG. 7 is a schematic diagram illustrating a modified circuit allowing efficient operation in the range of 2-9 MHz according to an embodiment of the invention.

FIG. 7 is a schematic representation of the induction oscillator circuit 700 for use in the frequency range of 2-9 MHz in accordance with another embodiment of the invention. As in the prior art, series capacitors 703 and 707 form a set ratio in order to set a predetermined feedback amplitude. By placing capacitor 704 directly in parallel with the induction coil 705, a majority of the resonant current will be controlled by capacitor 704. The resonant frequency can be primarily determined by the combination of capacitor 704 and the induction coil 705. A great advantage of this circuit is that a smaller value of capacitance can now be used for capacitors 703 and 707. Moreover, these capacitors can also be physically smaller in size since they need not handle such high currents. With this implementation, the resonant frequency is set independently of the feedback amplitude.

In use, the input power level is well controlled for this analytical application. If the power level is too low, for example less than one kilowatt, (<1 kW) the sample will not melt and combust. If the power level is substantially high, for example greater than three kilowatts (>3 kW) the sample heats too quickly and splatters and the analytical results will not be accurate. Thus, an advantage of the present invention is this method of applying a predetermined power at the predetermined frequency with the proper amount of accelerator yields very consistent and favorable results.

Figure 8:
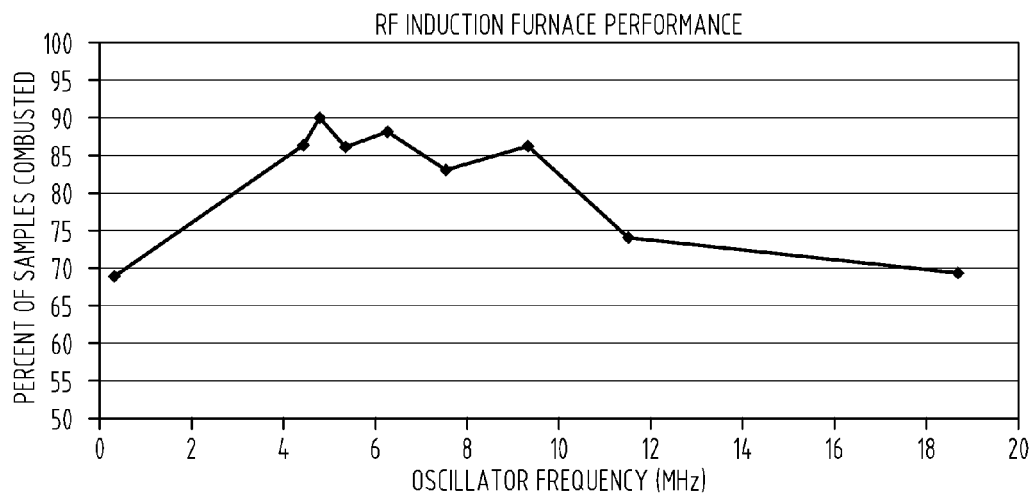
FIG. 8 is a graph illustrating the percentage of the sample combusted versus the frequency of the RF oscillator in the induction furnace.

FIG. 8 is a graph illustrating the percentage of the sample combusted versus the frequency of the RF oscillator in the induction furnace. Each data point on the graph is an average, comprised of several sample types and varying amounts of accelerator. The graph illustrates a combustion furnace operating in a range between approximately 300 kHz-19 MHz. In this range, the most efficient combustion of metallic samples unexpectedly occurs at approximately 4.5 MHz where about ninety percent (90%) of the samples are fully combusted. This decreases slowly reaching about sixty-eight percent (68%) of the samples burned at 19 MHz. Operation at 300 kHz show that accelerator will not combust and will not melt either powder or chip samples. Thus, the method used in the present invention operates in a frequency range that is high enough in frequency to combust the accelerator yet low enough in frequency to combust pins and disks of sample material.

With the induction furnace operated at approximately 4.5 MHz, nearly all samples can be completely combusted without accelerator and all samples will combust with accelerator. In use, the degree of splatter without accelerator may prevent accurate analysis of the sample. Approximately ½ gram of accelerator is required to reduce splatter and maintain combustion on difficult samples. Hence, the invention offers an unexpected result operating in this range and particularly at approximately 4.5 MHz since approximately half of the amount of accelerator used as compared with processes used in the prior art. As compared to the prior art, the present method is faster since fewer burns need to be repeated to obtain accurate results. This method is less expensive since less accelerator is combusted during each test and because this method requires fewer repeated tests. This method is also more accurate since less operator intervention is required to determine if the level of combustion was adequate.

Thus, the method of the present invention used in an induction furnace for combusting samples of conductive materials using a reduced amount of accelerator. This process includes combusting accelerator material to determine the amount of analyte in the accelerator and providing a crucible for holding a sample within the induction furnace. Less than one gram (1 g) of accelerator material is inserted into the crucible with the sample and the induction furnace is activated for some predetermined time period. The induction furnace is operated in an RF frequency range between 2-9 MHz at a power level between approximately 1 kW and 3 kW input power for combusting the sample but in some cases no accelerator is needed if operated at approximately 4.5 MHz.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A method used with an analytical induction furnace instrument for providing consistent combustion of sample materials with a diminished amount of accelerator comprising the steps of:
   providing a crucible for holding a sample within the induction furnace;
   inserting less than one and one half gram of accelerator material into the crucible with the sample;
   actuating the induction furnace at a single resonant frequency using an oscillator such that a generator frequency is identical to an induction frequency of operation for a predetermined time period; and
   wherein the induction furnace is actuated in an RF frequency range between 2-9 MHz for combusting the sample.

2. A method used with an induction furnace as in claim 1, further comprising the step of:
   oscillating the analytical induction furnace at approximately 4.5 MHz.

3. A method used with an induction furnace as in claim 1, wherein the crucible is manufactured of a ceramic material.

4. A method used with an induction furnace as in claim 1, wherein the induction furnace operates in a range between 1 kW and 3 kW input power.

5. A method used with the induction furnace as in claim 1, further comprising the step of:
   providing an induction oscillator circuit utilizing a first capacitance comprised of a plurality of series connected capacitors and a second capacitance connected in parallel with the first capacitance such that the first capacitance and second capacitance are parallel connected with an induction coil.

6. A method used with the induction furnace as in claim 1, wherein the sample is combusted in a high oxygen environment.

7. A method for use in an induction furnace analytical instrument for combusting samples of conductive materials using a diminished amount of accelerator comprising the steps of:
   combusting accelerator material to determine the amount of analyte in the accelerator;
   providing a crucible for holding a sample within the induction furnace;
   inserting less than one gram of accelerator material into the crucible with the sample;
   actuating the induction furnace using an oscillator having an ungrounded coil and at least one parallel capacitance for operating the oscillator at a single resonant frequency such that a generator frequency of the oscillator is identical to an induction frequency of operation for a predetermined time period; and
   wherein the induction furnace is actuated in an RF frequency range between 2-9 MHz and between 1 kW-3 kW input power for combusting the sample.

8. A method for use in an induction furnace as in claim 7, further comprising the step of:
   oscillating the induction furnace at frequency of approximately 4.5 MHz.

9. A method for use in an induction furnace as in claim 7, wherein the sample is combusted in a high oxygen environment.

10. A method for use in an induction furnace as in claim 7, further comprising the step of:
    providing an induction oscillator circuit for providing an RF voltage to the sample.

11. A method for use in an induction furnace as in claim 10, wherein the induction oscillator includes a first capacitance and a second capacitance parallel connected with an induction coil.

12. A method for analytical testing of conductive materials in an induction furnace comprising the steps of:
    providing a ceramic crucible having no accelerator for holding a sample within the induction furnace;
    actuating the induction furnace using an oscillator having an ungrounded coil and at least one parallel capacitance for operating the oscillator at a single resonant frequency such that a generator frequency of the oscillator is identical to an induction frequency of operation for a predetermined time period so an analyte is combusted from the sample; and
    wherein the induction furnace operates at an RF frequency range between 2-9 MHz at approximately 2 kW input power for thoroughly melting the sample for use in an analytical instrument.

13. A method used for analytical testing conductive materials as in claim 12, further comprising the step of:
    providing an induction oscillator circuit in the induction furnace utilizing a first capacitance comprised of a plurality of capacitors for setting a feedback ratio and a second capacitance connected in parallel with the first capacitance such that the first capacitance and second capacitance are parallel connected with an induction coil.

14. A method used for analytical testing conductive materials as in claim 12, further comprising the step of:
    operating the induction furnace at approximately 4.5 MHz.

15. A method used for analytical testing conductive materials as in claim 12, further comprising the step of:
    combusting the sample in a high oxygen environment.

* * * * *